United States Patent
Yazawa et al.

(10) Patent No.: US 8,088,744 B2
(45) Date of Patent: Jan. 3, 2012

(54) CHOLESTANOL DERIVATIVE FOR COMBINED USE

(75) Inventors: Shin Yazawa, Osaka (JP); Toyo Nishimura, Osaka (JP); Takayuki Asao, Maebashi (JP)

(73) Assignees: Otsuka Pharmaceutical Co., Ltd., Tokyo (JP); National University Corporation Gunma University, Maebashi-shi (JP)

( * ) Notice: Subject to any disclaimer, the term of this patent is extended or adjusted under 35 U.S.C. 154(b) by 0 days.

(21) Appl. No.: 12/553,355

(22) Filed: Sep. 3, 2009

(65) Prior Publication Data

US 2010/0062053 A1   Mar. 11, 2010

Related U.S. Application Data

(63) Continuation of application No. PCT/JP2009/000985, filed on Mar. 4, 2009.

(30) Foreign Application Priority Data

Mar. 5, 2008 (JP) ................................. 2008-055284

(51) Int. Cl.
*A61K 31/704* (2006.01)
*A61K 31/724* (2006.01)
*A61K 9/127* (2006.01)
*A61K 33/24* (2006.01)

(52) U.S. Cl. ............ 514/26; 514/58; 514/492; 514/778; 424/450; 424/649

(58) Field of Classification Search ................... None
See application file for complete search history.

(56) References Cited

U.S. PATENT DOCUMENTS

| 2006/0193903 A1 | 8/2006 | Yazawa et al. |
| 2007/0244112 A1 | 10/2007 | Pekari et al. |

FOREIGN PATENT DOCUMENTS

| CN | 1822844 | 3/2007 |
| JP | 11-60592 | 3/1999 |
| JP | 11-060592 | 3/1999 |
| JP | 2000-191685 | 7/2000 |
| WO | 2005-007172 | 1/2005 |
| WO | 2005-118071 | 12/2005 |
| WO | 2007-026869 | 3/2007 |

OTHER PUBLICATIONS

Andre, T. et al "Current issues in adjuvant treatment of stage II colon cancer" Ann. Surg. Oncol. (2006) vol. 13, 6, pp. 887-898.*
Agarwal, B. et al "Lovastatin augments apoptosis induced by chemotherapeutic ..." Clin. Cancer Res. (1999) vol. 5, pp. 2223-2229.*
Sim, B. et al "Angiostatin and endostatin ... " Cancer and Metastasis Rev. (2000) vol. 19, pp. 181-190.*
International Preliminary Report dated Oct. 21, 2010 as received in the corresponding PCT/JP2009/000985 application. All cited references have been previously filed on Sep. 3, 2009.
Guo Hua, et al. "Pharmatology", Hubei Sciene and Technology Press, pp. 261-262, Mar. 31, 2007 w/English Translation.
Chinese Office Action dated Apr. 26, 2011 as received in the corresponding Chinese Patent Application No. 200980000193.8.

* cited by examiner

*Primary Examiner* — Leigh Maier
(74) *Attorney, Agent, or Firm* — Oblon, Spivak, McClelland, Maier & Neustadt, L.L.P.

(57) ABSTRACT

The invention provides a cancer chemotherapeutic agent which has fewer side effects and excellent efficacy. The cancer chemotherapeutic agent of the invention includes a cholestanol derivative represented by formula (1):

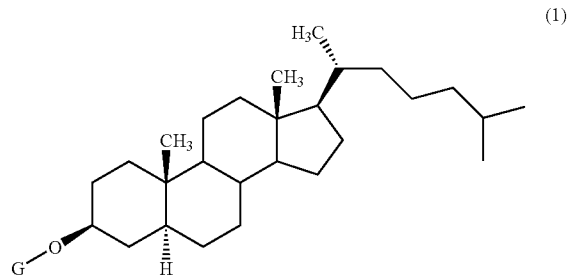

(wherein G represents GlcNAc-Gal-, GlcNAc-Gal-Glc-, Fuc-Gal-, Gal-Glc-, Gal-, or GlcNAc-) or a cyclodextrin inclusion compound thereof, and an anti-cancer agent.

7 Claims, 11 Drawing Sheets

- - - : Control
- - - - - : CDDP 0.1 μ mol (Day 2)
———— : GC-CD 0.5 μM (Day 2 + Day 3)
▬▬▬ : CDDP 0.1 μM (Day 2) + GC-CD 0.5 μM (Day 2 + Day 3)

$P < 0.001$ (vs. UT, GC)

Fig. 10-A
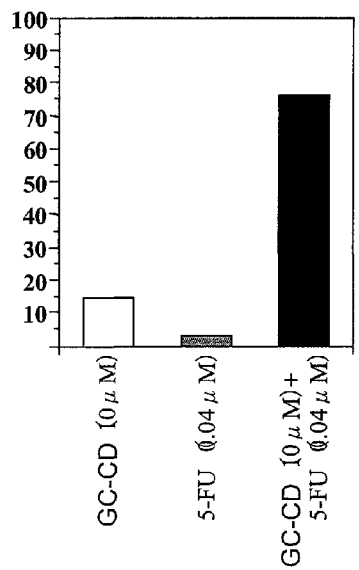
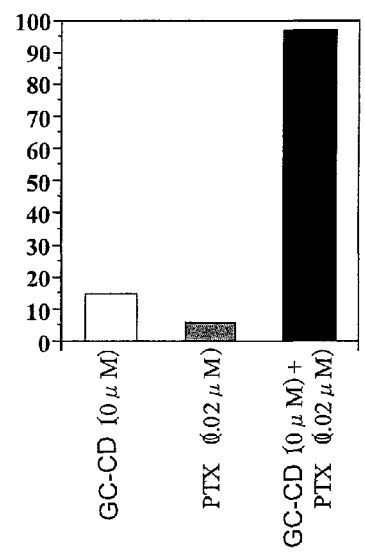
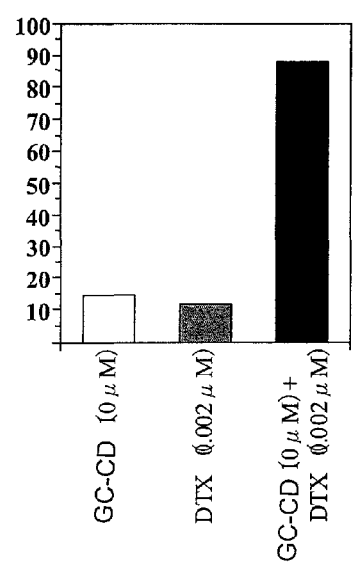
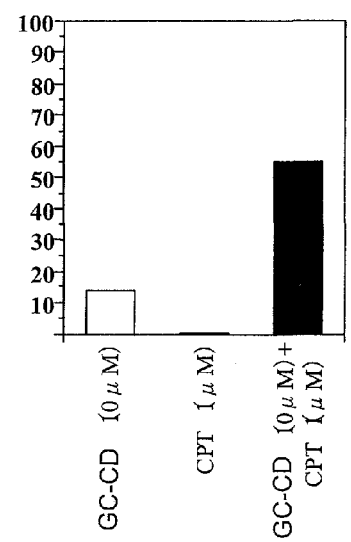

Fig. 10-B
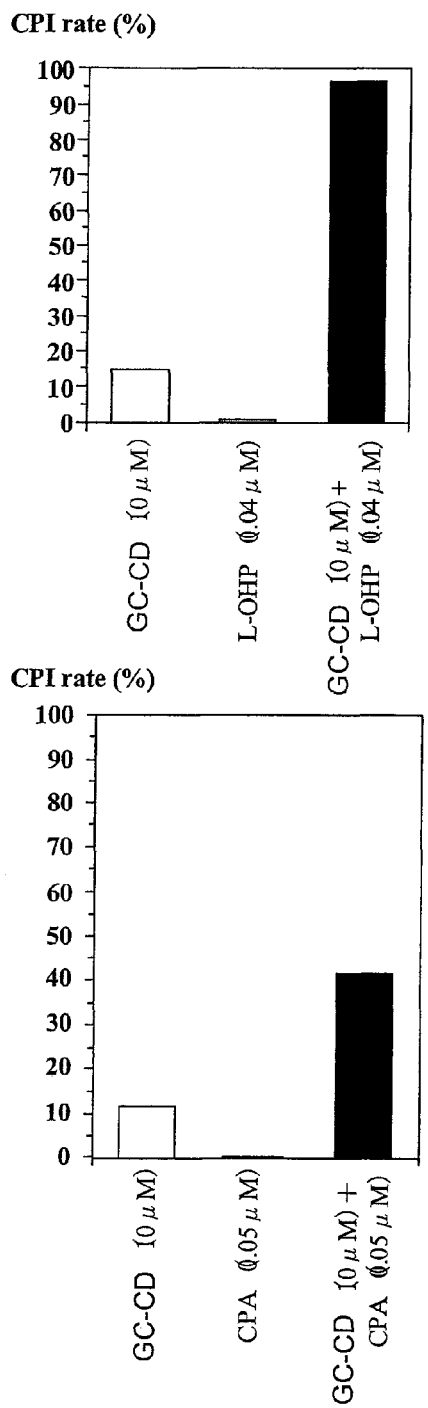

CHOLESTANOL DERIVATIVE FOR COMBINED USE

CROSS-REFERENCE TO RELATED APPLICATIONS

This application is a continuation of PCT/JP09/00985 filed Mar. 4, 2009 and claims the benefit of JP 2008-055284 filed Mar. 5, 2008.

BACKGROUND OF THE INVENTION

1. Field of the Invention

The present invention relates to a chemotherapeutic agent for cancer (hereinafter referred to as a "cancer chemotherapeutic agent") and, more particularly, to a cancer chemotherapeutic agent employing a cholestanol derivative and an anti-cancer agent in combination.

2. Background Art

A variety of anti-cancer agents used in chemotherapy for cancer, which is one mode of cancer therapy, have hitherto been developed and classified based on structure, action mechanism, etc. However, the efficacy of such an anti-cancer agent employed as a single agent is unsatisfactory. Instead, multi-drug therapy employing a plurality of anti-cancer agents has been predominantly carried out in recent years from the viewpoint of suppressing adverse side effects, and the efficacy of multi-drug therapy has been recognized.

Under such circumstances, both of the development of new anti-cancer combination chemotherapy, which has fewer adverse side effect and higher efficacy than conventional chemotherapies, and the development of new chemotherapeutic agents for use in the chemotherapy are desired.

Meanwhile, a cholestanol derivative, in which a sugar chain such as GlcNAc-Gal-, GlcNAc-Gal-Glc-, Fuc-Gal-, Gal-Glc, Gal-, or GlcNAc- is bonding to cholestanol (the compound that the double bond in the B ring of the cholesterol is saturated), were previously found to have excellent anti-tumor activity. JP-A-2000-191685, JP-A-1999-60592, WO 2005/007172 (pamphlet), and WO 2007/026869 (pamphlet) disclose the effects of such cholestanol derivatives.

However, no cases have been reported in which the aforementioned cholestanol derivatives and another anti-cancer agent are employed in combination.

SUMMARY OF THE INVENTION

Thus, the present invention is directed to provision of a cancer chemotherapeutic agent which has fewer side effects and excellent efficacy.

In view of the foregoing, the present inventors have carried out extensive studies, and have found that a remarkably potentiated anti-cancer effect can be attained through employment, in combination, of a cholestanol derivative represented by formula (1) or a cyclodextrin inclusion compound thereof and a known chemotherapeutic agent (anti-cancer agent), and thus the combined use of these pharmaceutical agents in cancer chemotherapy is very useful.

Accordingly, the present invention is directed to the following (1) to (10).

(1) A cancer chemotherapeutic agent comprising, in combination, a cholestanol derivative represented by formula (1):

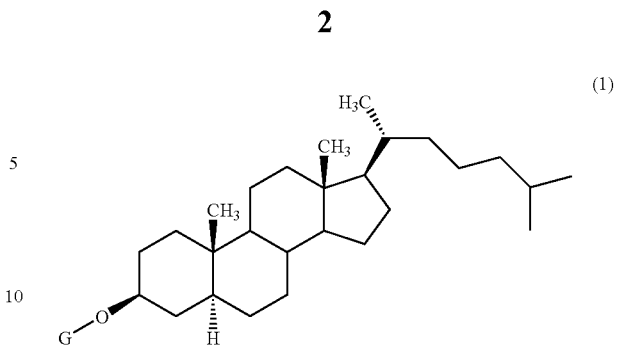

(wherein G represents GlcNAc-Gal-, GlcNAc-Gal-Glc-, Fuc-Gal-, Gal-Glc-, Gal-, or GlcNAc-) or a cyclodextrin inclusion compound thereof, and an anti-cancer agent.

(2) A cancer chemotherapeutic agent according to (1) above, wherein, in formula (1), G is GlcNAc-Gal- or GlcNAc-.

(3) A cancer chemotherapeutic agent according to (1) or (2) above, wherein the anti-cancer agent is one or more species selected from the group consisting of a taxane anti-cancer agent, a platinum complex anti-cancer agent, a pemetrexed compound, and fluorouracil.

(4) A cancer chemotherapeutic agent according to (3) above, wherein the anti-cancer agent is one or more species selected from the group consisting of Paclitaxel, Docetaxcel, Pemetrexed, 5-FU, Cisplatin, Oxaliplatin, Cyclophosphamide, and Irinotecan.

(5) A cancer chemotherapeutic agent according to any of (1) to (4) above, which is a compounding agent.

(6) A cancer chemotherapeutic agent according to any of (1) to (4) above, which is in the form of a kit including a drug containing a cholestanol derivative and a drug containing an anti-cancer agent.

(7) A cancer chemotherapeutic agent according to (6) above, wherein the drug containing a cholestanol derivative is a liposomal formulation.

(8) Use, in combination, of a cholestanol derivative represented by formula (1):

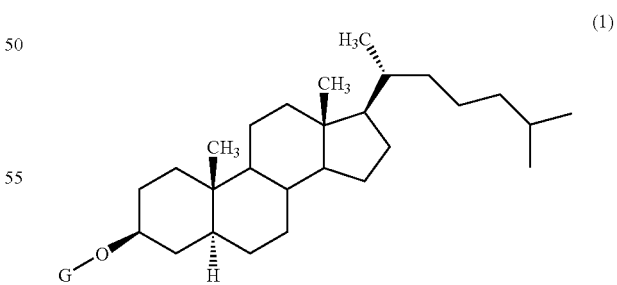

(wherein G represents GlcNAc-Gal-, GlcNAc-Gal-Glc-, Fuc-Gal-, Gal-Glc-, Gal-, or GlcNAc-) or a cyclodextrin inclusion compound thereof and an anti-cancer agent, for producing a cancer chemotherapeutic agent.

(9) A cancer chemotherapy, characterized by comprising administering, in combination, a cholestanol derivative represented by formula (1):

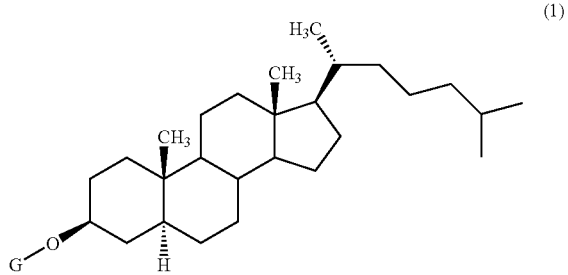

(wherein G represents GlcNAc-Gal-, GlcNAc-Gal-Glc-, Fuc-Gal-, Gal-Glc-, Gal-, or GlcNAc-) or a cyclodextrin inclusion compound thereof and an anti-cancer agent, to a patient in need thereof.

(10) A cancer chemotherapy according to (9) above, wherein the cholestanol derivative or a cyclodextrin inclusion compound thereof and the anti-cancer agent are administered to a patient in need thereof simultaneously, or separately at intervals.

Through employment of the cancer chemotherapeutic agent and the cancer chemotherapy according to the present invention, prevention and treatment of cancer can be realized with safety and higher efficacy.

BRIEF DESCRIPTION OF THE DRAWINGS

FIG. 10-A is a graph showing the cell proliferation inhibitory effects of an anti-cancer agent (5-FU, PTX, DTX, or CPT), GC-CD, and the anti-cancer agent+GC-CD on colon 26 cells; and FIG. 10-B is a graph showing the cell proliferation inhibitory effects of an anti-cancer agent (L-OHP or CPA), GC-CD, and the anti-cancer agent+GC-CD on colon 26 cells.

DETAILED DESCRIPTION OF PREFERRED EMBODIMENTS

Figure 1:
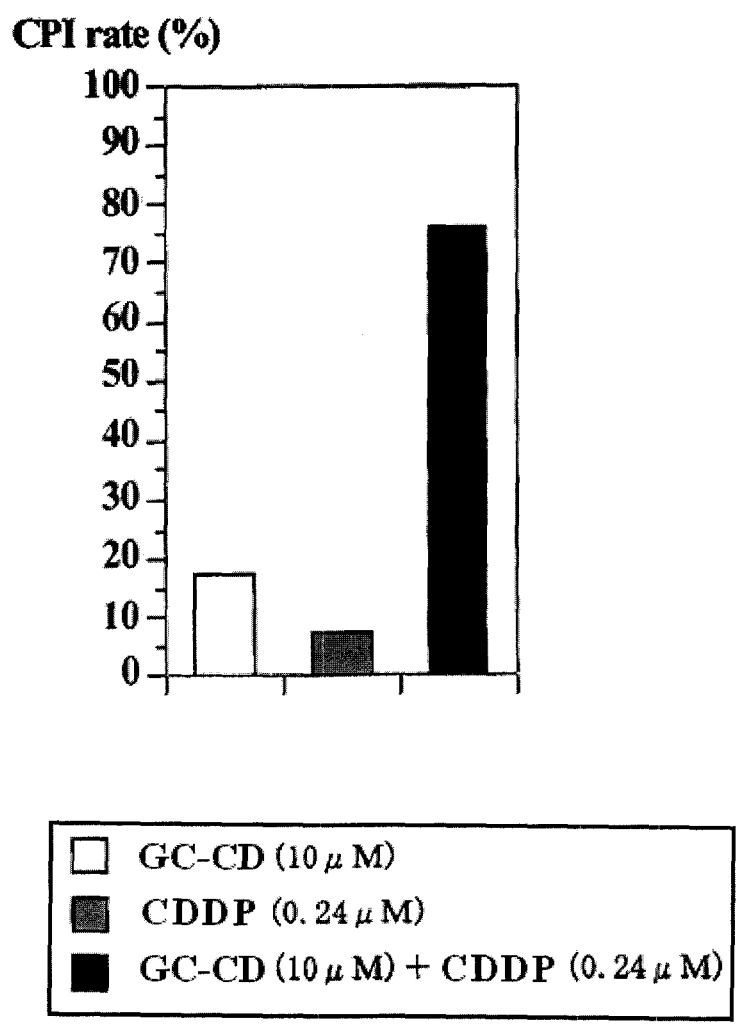
FIG. 1 is a graph showing the cell proliferation inhibitory effects of CDDP, GC-CD, and CDDP+GC-CD on colon 26 cells.

The specific cholestanol derivatives represented by formula (1) and employed in the present invention are all known compounds.

Among the cholestanol derivatives which are represented by formula (1) and in which G is GlcNAc-Gal-, G is preferably GlcNAcβ1,3-Galβ- or GlcNAcβ1,4-Galβ-. Among the cholestanol derivatives (1) in which G is GlcNAc-Gal-Glc-, G is preferably GlcNAcβ1,3-Galβ1,4-Glc-. Among the cholestanol derivatives (1) in which G is Fuc-Gal-, G is preferably Fucα1,3Gal-. Among the cholestanol derivatives (1) in which G is Gal-Glc-, G is preferably Galβ1,4Glcβ-. Among the cholestanol derivatives (1) in which G is Gal-, G is preferably Galβ-. Among the cholestanol derivatives (1) in which G is GlcNAc-, G is preferably GlcNAcβ-.

Of these, species in which G is GlcNAc-Gal- and GlcNAc- are more preferred, with those in which G is GlcNAcβ1,4-Galβ- and GlcNAcβ- being still more preferred.

The aforementioned cholestanol derivatives may be produced through a method, for example, disclosed in the aforementioned Patent Documents or a similar method.

The cholestanol derivative represented by (1) readily forms an inclusion complex with a cyclodextrin or a derivative thereof. Thus, the cholestanol derivative employed in the present invention may be a cyclodextrin inclusion compound thereof. In formation of such inclusion compounds, the size of the guest molecule to be included, Van der Waals interaction between the guest molecule and cyclodextrin, and hydrogen bond between the hydroxyl groups of cyclodextrin and the guest molecule must be taken into consideration. Therefore, insoluble guest compounds do not always form the corresponding inclusion compounds. However, the cholestanol derivative of the present invention can form good inclusion complexes with cyclodextrin.

Examples of the cyclodextrin forming the cyclodextrin inclusion compound of the present invention include cyclodextrins such as α-cyclodextrin, β-cyclodextrin, and γ-cyclodextrin; and cyclodextrion derivatives such as methyl-β-cyclodextrin, 2-hydroxypropyl-β-cyclodextrin, monoacetyl-β-cyclodextrin, and 2-hydroxypropyl-γ-cyclodextrin. Of these, 2-hydroxypropyl-β-cyclodextrin is preferred for obtaining improved solubility.

The cyclodextrin inclusion compound may be prepared through, for example, the following procedure: an aqueous solution of a cyclodextrin or a derivative thereof having an appropriate concentration (e.g., 20 to 40%) is prepared, and the cholestanol derivative of the present invention is added to the aqueous solution, followed by stirring of the resultant mixture.

No particular limitation is imposed on the concentration of the solution of the cholestanol derivative (1), so long as the cholestanol derivative can form an inclusion compound with cyclodextrin. Generally, the concentration is about 1 to about 50 mass %, preferably about 10 to about 30 mass %.

The thus-produced cyclodextrin inclusion compound is highly water-soluble and, therefore, effectively exhibits the effect of the guest in vivo. Another advantage of the cyclodextrin inclusion compound is to ensure consistent in vitro test results.

Alternatively, the cholestanol derivative (1) may be prepared into a liposomal formulation, whereby the cholestanol derivative can be more effectively delivered to the action expression site. Another advantage of the cyclodextrin inclusion compound is to ensure consistent in vitro test results.

Preferably, the liposomal formulation includes the cholestanol derivative of the present invention, a membrane component, and an aliphatic or aromatic amine.

The cholestanol derivative content in the liposomal formulation is preferably 0.3 to 2.0 mol, more preferably 0.8 to 1.5 mol, with respect to 1 mol of the membrane component.

The membrane component may be a phospholipid. Specific examples of preferably employed phospholipids include natural and synthetic phospholipids such as phosphatidylcholine, phosphatidylethanolamine, phosphatidylserine, phosphatidylinositol, and phosphatidic acid; mixtures thereof; and modified natural phospholipids such as aqueous lecithin. Examples of more preferred species include phosphatidylcholine (1α-dipalmitoylphosphatidylcholine (DPPC)).

The aliphatic or aromatic amine is employed mainly for positively charging the surface of lipid membrane. Examples of such amines include aliphatic amines such as stearylamine and oleylamine; and aromatic amines such as fluorenethylamine. Among them, stearylamine is particularly preferably employed.

Preferably, the amine is contained in an amount of 0.04 to 0.15 mol, more preferably 0.1 to 0.15 mol, with respect to 1 mol of membrane component (phospholipid).

In addition to the aforementioned components, if required, the liposome may further contain a membrane structure stabilizer such as cholesterol, fatty acid, diacetyl phosphate, etc.

The aqueous solution employing for dispersing the membrane component is preferably water, physiological saline, buffer, aqueous sugar solution, or a mixture thereof. Either an organic or an inorganic buffer may be used, so long as the buffer has a buffering action in the vicinity of the hydrogen ion concentration of body fluid. Examples of such buffers include a phosphate buffer.

No particular limitation is imposed on the method of preparing the liposomal formulation, and generally employed methods may be selected. Examples of the employable method include methods disclosed in JP-A-1982-82310, JP-A-1985-12127, JP-A-1985-58915, JP-A-1989-117824, JP-A-1989-167218, JP-A-1992-29925, and JP-A-1997-87168; a method disclosed in Methods of Biochemical Analysis (1988) 33, p. 337; or a method disclosed in "Liposome" (published by Nankodo).

No particular limitation is imposed on the anti-cancer agent which is used in combination with the cholestanol derivative represented by formula (1) or a cyclodextrin inclusion compound thereof, and known cancer chemotherapeutic agents may be used. Standard therapeutic agents which have been established with respect to the cancer of therapy target are preferably employed.

Specific examples include alkylating agents such as Cyclophosphamide, Ifosfamide, Melphalan (L-PAM), Busulfan, and Carboquione; metabolism antagonists such as 6-Mercaptopurine (6-MP), Methotrexate (MTX), 5-Fluorouracil (5-FU), Tegafur, Enocitabine (BHAC), and pemetrexed compounds (Pemetrexed, Alimta, MTA), etc.; carcinostatic antibiotics such as Actinomycin D, Daunorubicin, Bleomycin, Peplomycin, Mitomycin C, Aclarubicin, and Neocarzinostatin (NCS); plant alkaloids such as Vincristine, Vindesine, Vinblastine, taxane anti-cancer agents (Taxotere (Docetaxel) and Taxol (Paclitaxel, TXL), etc.), and Irinotecan (CPT-11); and platinum compounds such as Cisplatin (CDDP), and Carboplatin, Oxaliplatin (L-OHP). These anti-cancer agents may be used singly or in combination of two or more species.

As shown in the Examples described hereinbelow, when the cholestanol derivative represented by formula (1) or a cyclodextrin inclusion compound thereof is used in combination with an anti-cancer agent, proliferation of cancer cells of various types are strongly suppressed, as compared with the case of administration of only each agent. Therefore, this combined chemotherapy can drastically enhance therapeutic efficacy and mitigation of adverse side effects, and a pharmaceutical product containing these ingredients is a useful cancer chemotherapeutic agent.

No particular limitation is imposed on the cancer which can be effectively treated by administering the cancer chemotherapeutic agent of the present invention. Examples of the target cancer include malignant tumors such as gastric cancer, large bowel cancer, pancreatic cancer, uterus cancer, ovaria cancer, lung cancer, gallbladder cancer, esophageal cancer, liver cancer, breast cancer, mesothelioma, and prostatic cancer.

The form of the cancer chemotherapeutic agent of the present invention may be a compounding agent in which the aforementioned ingredients are mixed at an appropriate ratio, each at an effective amount, to form a single dosage form (single-formulation type), or may be a kit that consists of the respective dosage form of the aforementioned ingredients, each of which is formed independently including each effective amount, and that enables the dosage forms to be administered simultaneously or separately at intervals (double-formulation type).

Similar to general pharmaceutical formulations, no particular limitation is imposed on the dosage form of the above-described formulation, and the form may be any of the solid form such as tablet, liquid form such as injection, dry powder dissolving before use, etc.

No particular limitation is imposed on the administration route of the formulation, and an appropriate route may be determined depending on the dosage form of the agents. For example, an injection solution may be administered intravenously, intramuscularly, subcutaneously, intradermally, or interperitoneally, and a solid form may be administered orally or enterally.

The formulation may be prepared through a known method in the art. All pharmaceutically acceptable carriers (excipients or diluents such as a filler, a bulking agent, and a binder) generally employed in the art may also be employed.

For example, a peroral solid form may be prepared through mixing the drug ingredients of the present invention with a excipient, and with an optional binder, disintegrant, lubricant, colorant, flavoring agent, deodorant, etc., and forming the mixture into tablets, coated-tablets, granules, powder, capsules, etc. through a method known in the art. These additive may be those generally employed in the art. Examples of the excipient include lactose, sucrose, sodium chloride, glucose, starch, calcium carbonate, kaolin, microcrystalline cellulose, and silicic acid. Examples of the binder include water, ethanol, propanol, simple syrup, liquid glucose, liquid starch, liquid gelatin, carboxymethyl cellulose, hydroxypropyl cellulose, hydroxypropyl starch, methyl cellulose, ethyl cellulose, shellac, calcium phosphate, and polyvinylpyrrolidone. Examples of the disintegrant include dry starch, sodium alginate, agar powder, sodium hydrogencarbonate, calcium carbonate, sodium lauryl sulfate, monoglyceryl stearate, and lactose. Examples of the lubricant include purified talc, stearate salts, borax, and polyethylene glycol. Examples of the flavoring agent include sucrose, orange peel, citric acid, and tartaric acid.

An oral liquid formulation may be prepared by mixing the drug ingredients of the present invention with a flavoring agent, buffer, stabilizer, deodorant, etc., and forming the mixture into internal liquid agent, syrup, elixir, etc. through a method known in the art. The flavoring agent employed in the preparation may be any of the aforementioned members. Examples of the buffer include sodium citrate. Examples of the stabilizer include traganth, gum arabic, and gelatin.

Injection solutions may be prepared by mixing the drug ingredients of the present invention with additives such as a pH-regulator, buffer, stabilizer, tonicity agent, and local anesthetic agent, etc., and forming the mixture through a method known in the art, to thereby provide subcutaneous, intramuscular, and intravenous injection liquids. Examples of the pH-regulator and buffer include sodium citrate, EDTA, thioglycolic acid, and thiolactic acid. Examples of the local anesthetic include procaine hydrochloride and lidocaine hydrochloride. Examples of the tonicity agent include sodium chloride and glucose.

Suppositories may be prepared by mixing the drug ingredients of the present invention with a carrier for formulation known in the art such as polyethylene glycol, lanolin, cacao butter, and fatty acid triglyceride, and with an optional surfactant such as Tween (registered trademark), and forming the mixture into suppositories through a method known in the art.

Ointments may be prepared by mixing the drug ingredients of the present invention with optional additives generally employed in the art such as a base, stabilizer, moisturizer, and preservatives, and forming the mixture into ointments through a method known in the art. Examples of the base include liquid paraffin, white petrolatum, white beeswax, octyldodecyl alcohol, and paraffin. Examples of the preservative include methyl p-hydroxybenzoate, ethyl p-hydroxybenzoate, and propyl p-hydroxybenzoate.

Cataplasms may be prepared by applying the aforementioned ointment, gel, cream, paste, etc. to a generally employed support through a routine method. Examples of appropriate supports include woven and nonwoven fabric made of cotton, staple fiber, or chemical fiber, and film and foamed sheet made of soft vinyl chloride, polyethylene, polyurethane, etc.

Generally, the formulation is preferably prepared so as to have a cholestanol derivative content and an anti-cancer agent content of 0.0001 to 80 wt. % (as effective ingredient).

When the cancer chemotherapeutic agent of the present invention is provided as a kit, the kit may be designed to pack independently the respective dosage form including separately the cholestanol derivative represented by formula (1) or a cyclodextrin inclusion compound thereof and an anti-cancer agent, each of which have been prepared in the above manner, and to be used each pharmaceutical formulation taken separately from the corresponding respective package before use. Alternatively, each pharmaceutical formulation may be held in a package suitable for each time of combined administration.

The dose of the cancer chemotherapeutic agent of the present invention varies depending on the body weight, age, sex, symptoms of a patient in need thereof, route and frequency of administration to a patient in need thereof, etc. Generally, for example, the daily dose for an adult is about 0.1 to 30 mg/kg as the cholestanol derivative (1), preferably 3 to 10 mg/kg. The dose of the anti-cancer agent may fall within a range established with respect to the agent, or may be lower than that range.

No particular limitation is imposed on the frequency of administration, and the agent may be administered once or several times a day. Single administration a day is preferred. When the kit is used, each of the formulation including separated drug ingredients may be administered simultaneously or intermittently.

EXAMPLES

The present invention will next be described in more detail by way of examples, which should not be construed as limiting the invention thereto.

Example 1

Effect of Drug Addition on Inhibition of Cancer Cell Proliferation

Colon26 cells (derived from mouse colon cancer) were inoculated to a 96-well plate ($1 \times 10^4$ cells/50 µL, 10% FCS-RPMI medium/well), and incubated at 37° C. for 16 hours. To each well, cisplatin (abbreviated as "CDDP") and/or a cyclodextrin inclusion compound (abbreviated as "GC-CD") of a cholestanol derivative in which G in formula (1) is GlcNAcβ- (abbreviated as "GC") was added (multi-fold dilution by FCS (−)-medium: final concentration: $\leqq 500$ µM, 50 µL), followed by incubation at 37° C. for two days. GC-CD was prepared in accordance with a method disclosed in Example 1(2) in WO 2007/026869. Specifically, a 40% aqueous solution of hydroxypropyl-β-cyclodextrin was prepared, and GC was added to the solution, followed by mixing with stirring (80° C. for 30 minutes), to thereby prepare GC-CD.

As a control, wells to which only FCS(−)-medium had been added were employed. Viable count was performed by means of a cell counting kit (product of Dojin).

Cell proliferation inhibition (CPI) rate (%) was calculated by the following equation. FIG. 1 shows the results.

$$CPI \text{ rate } (\%) = \left(1 - \frac{\text{treated cells } OD_{450-650}}{\text{untreated cells } OD_{450-650}}\right) \times 100$$

Example 2

Effect of Inhibition of Proliferation of Various Cancer Cells

Figure 2:
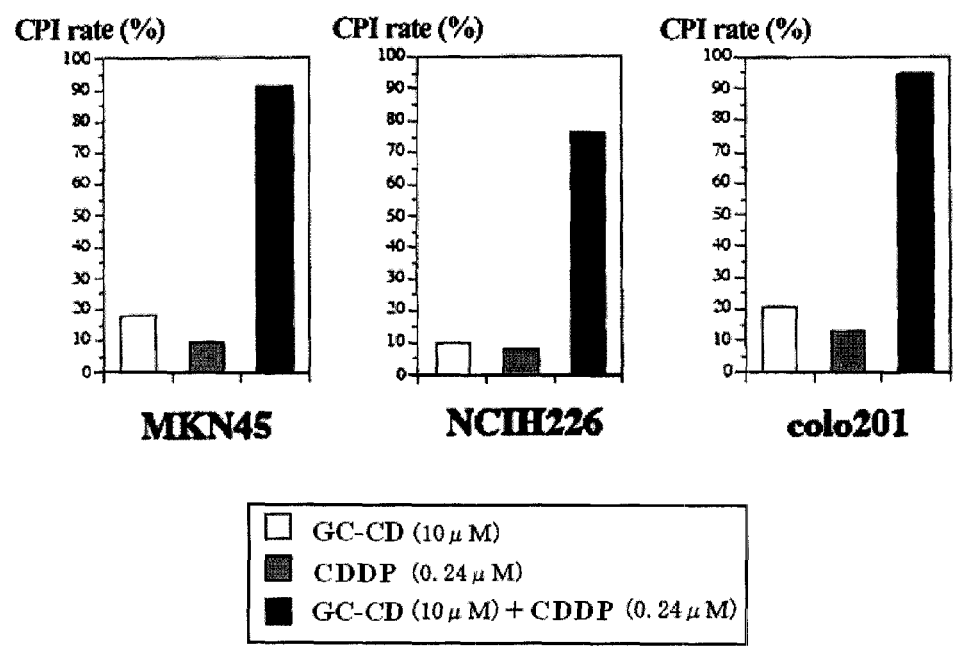
FIG. 2 is a graph showing the cell proliferation inhibitory effects of CDDP, GC-CD, and CDDP+GC-CD on MKN45 cells, NCIH226 cells, or colo201 cells.

The procedure of Example 1 was repeated, except that colon26 cells were changed to MKN45 (derived from human gastric cancer), NCIH226 (derived from human lung cancer), and Colo201 (derived from human colon cancer). CPI rate (%) was determined in a similar manner. FIG. 2 shows the results.

Figure 3:
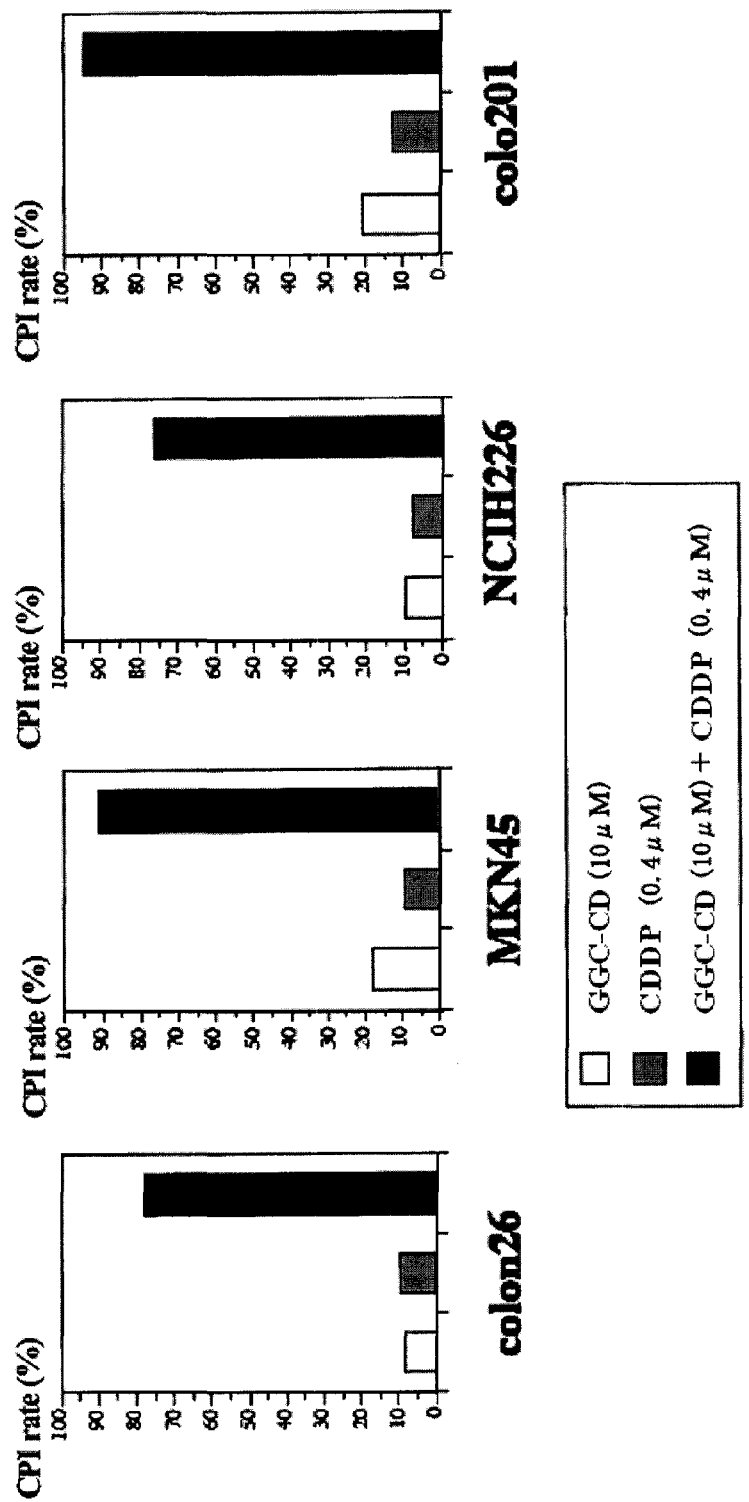
FIG. 3 is a graph showing the cell proliferation inhibitory effects of CDDP, GGC-CD, and CDDP+GGC-CD on colon26 cells, MKN45 cells, NCIH226 cells, or colo201 cells.

In Example 2, a cyclodextrin inclusion compound (abbreviated as "GGC-CD") of a cholestanol derivative in which G in formula (1) is GlcNAcβ1,4-Galβ- (abbreviated as "GGC") was also used. GGC-CD was produced in a manner similar to the method as the aforementioned GC-CD production method, except that the cholestanol compound was changed to GGC. CPI rate with respect to the cancer cells was determined. FIG. 3 shows the results.

Example 3

Effect of Drug Addition on Inhibition of Cancer Cell Proliferation In Vivo

In the following Examples, Balb/c mice (6-weeks old, female) were employed as test animals.

(1) Colon26 cells ($1\times10^4$ cells/mouse) were intraperitoneally inoculated to the mice (day 0). On the following day after inoculation (day 1), CDDP and/or GC-CD was adjusted with physiological saline (Otsuka normal saline) to a concentration of interest, and CDDP, GC-CD, or CDDP+GC-CD (500 μL) was intraperitoneally administered to the mice, followed by breeding. On day 19, mice were dissected, and the weight of the mesentery and the greater omentum was measured. To the control group, only physiological saline (500 μL) was administered (n=10; 10 mice/group).

Figure 4:
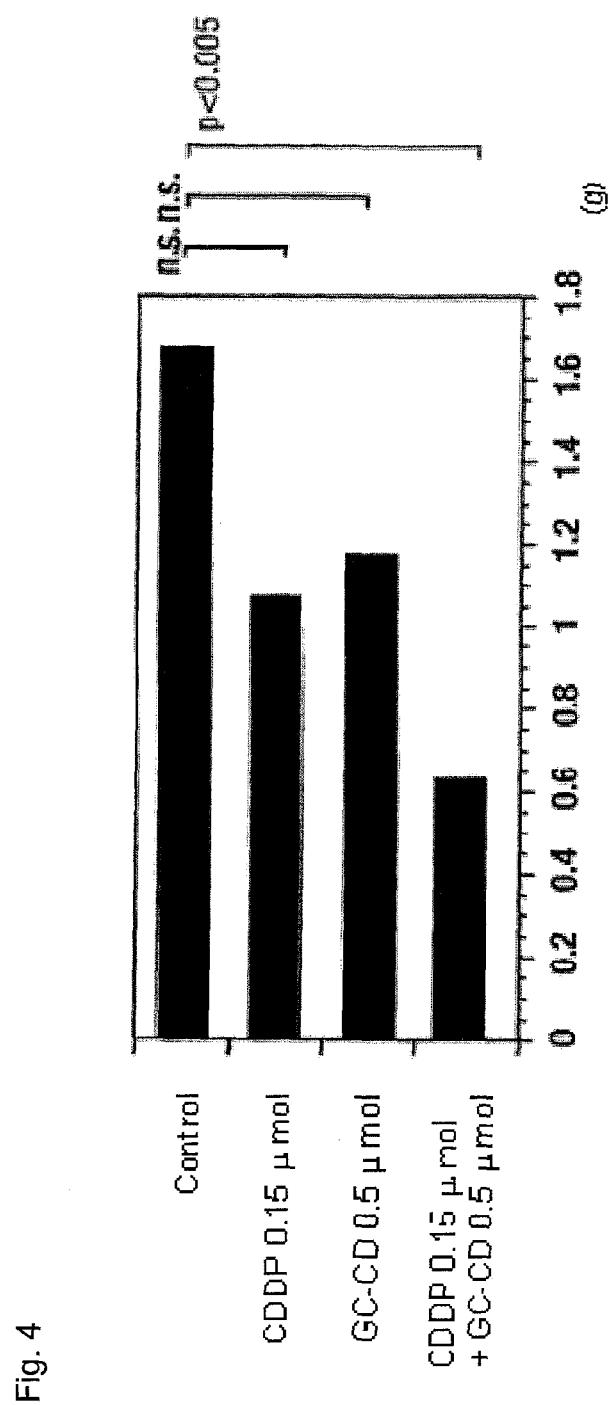
FIG. 4 is a graph showing the anti-tumor effect of single administration of CDDP, GC-CD, and CDDP+GC-CD against peritoneal dissemination caused by colon26 cells intraperitoneally inoculated in mice.

FIG. 4 shows the results.

(2) Colon26 cells ($1\times10^4$ cells/mouse) were intraperitoneally inoculated to the mice (day 0). On day 1, day 2, day 3, day 6, day 7, and day 8, CDDP and/or GC-CD was adjusted with physiological saline (Otsuka normal saline) to a concentration of interest, and CDDP, GC-CD, or CDDP+GC-CD (500 μL) was intraperitoneally administered to the mice, followed by breeding. On day 21, mice were dissected, and the weight of the mesentery and the greater omentum was measured. To the control group, only physiological saline (500 μL) was administered (n=10; 10 mice/group).

Figure 5:
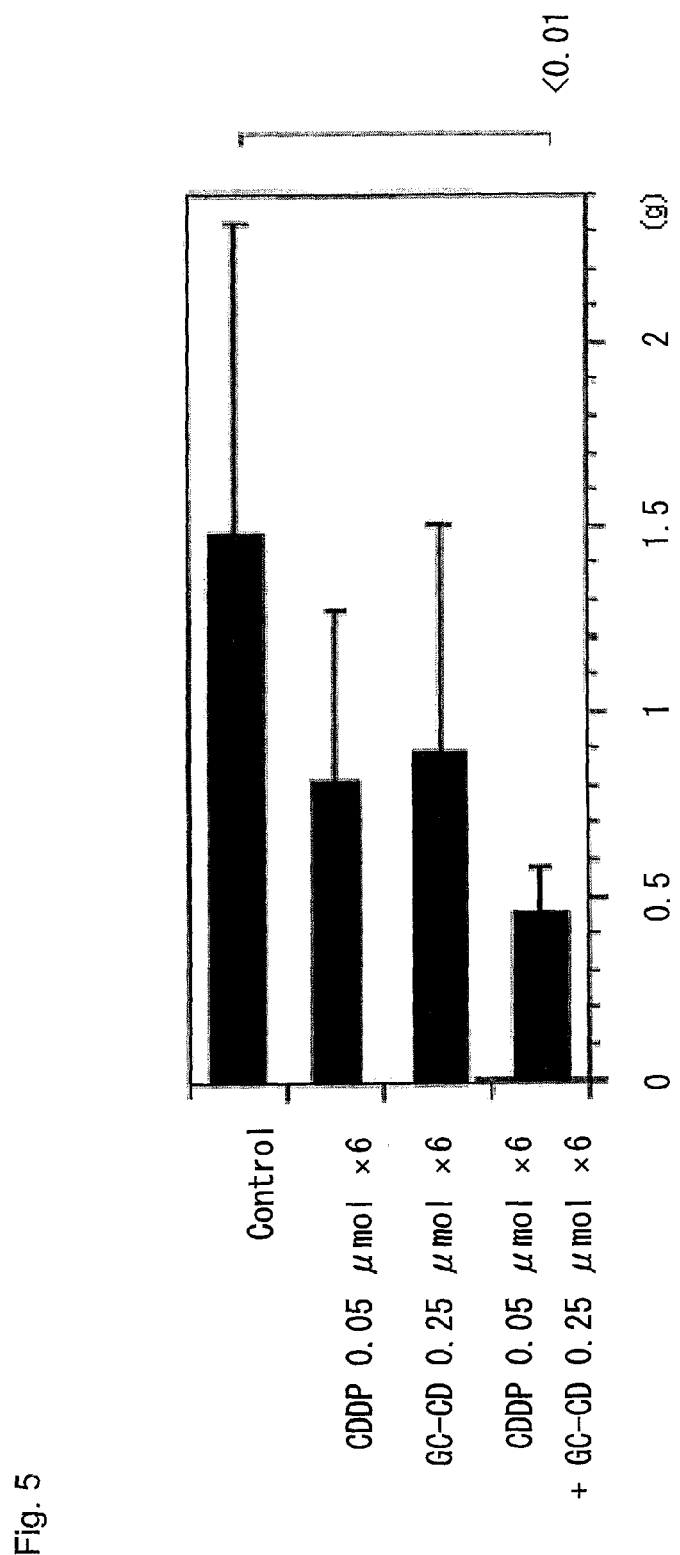
FIG. 5 is a graph showing the anti-tumor effect of multiple administration of CDDP, GC-CD, and CDDP+GC-CD against peritoneal dissemination caused by colon26 cells intraperitoneally inoculated in mice.

FIG. 5 shows the results.

(3) Colon26 cells ($1\times10^4$ cells/mouse) were intraperitoneally inoculated to the mice (day 0). On day 7, CDDP and/or GC-CD was adjusted with physiological saline (Otsuka normal saline) to a concentration of interest, and CDDP, GC-CD, or CDDP+GC-CD (500 μL) was intraperitoneally administered to the mice, followed by breeding. On day 18, mice were dissected, and the weight of the mesentery and the greater omentum was measured. To the control group, only physiological saline (500 μL) was administered (n=10; 10 mice/group).

Figure 6:
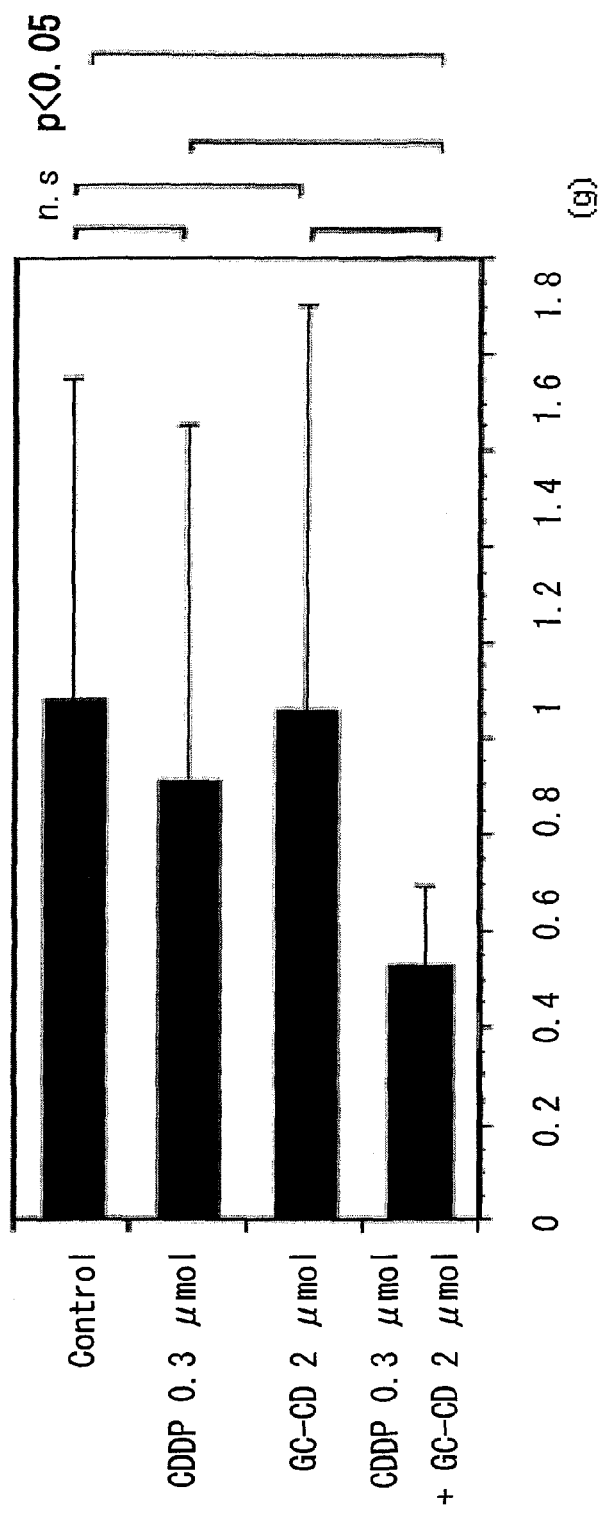
FIG. 6 is a graph showing the anti-tumor effect of single, delayed administration of CDDP, GC-CD, and CDDP+GC-CD against peritoneal dissemination caused by colon26 cells intraperitoneally inoculated in mice, after confirmation of peritoneal dissemination on the mesothelium of mice.

FIG. 6 shows the results.

Example 4

Anti-Tumor Effect By Drug Addition

Balb/c mice (6 weeks old, female) were employed as test animals. Colon26 cells ($1\times10^4$ cells/mouse) were intraperitoneally inoculated to the mice (day 0). On day 2 and/or day 3, CDDP and/or GC-CD was adjusted with physiological saline (Otsuka normal saline) to a concentration of interest, and CDDP (once, on day 2), GC-CD (twice, on day 2 and 3), or CDDP (once, on day 2)+GC-CD (twice, day 2 and 3) (500 μL) was intraperitoneally administered to the mice, followed by breeding. The survival duration (days) was counted to day 43. To the control group, only physiological saline (500 μL) was administered (n=10; 10 mice/group).

Figure 7:
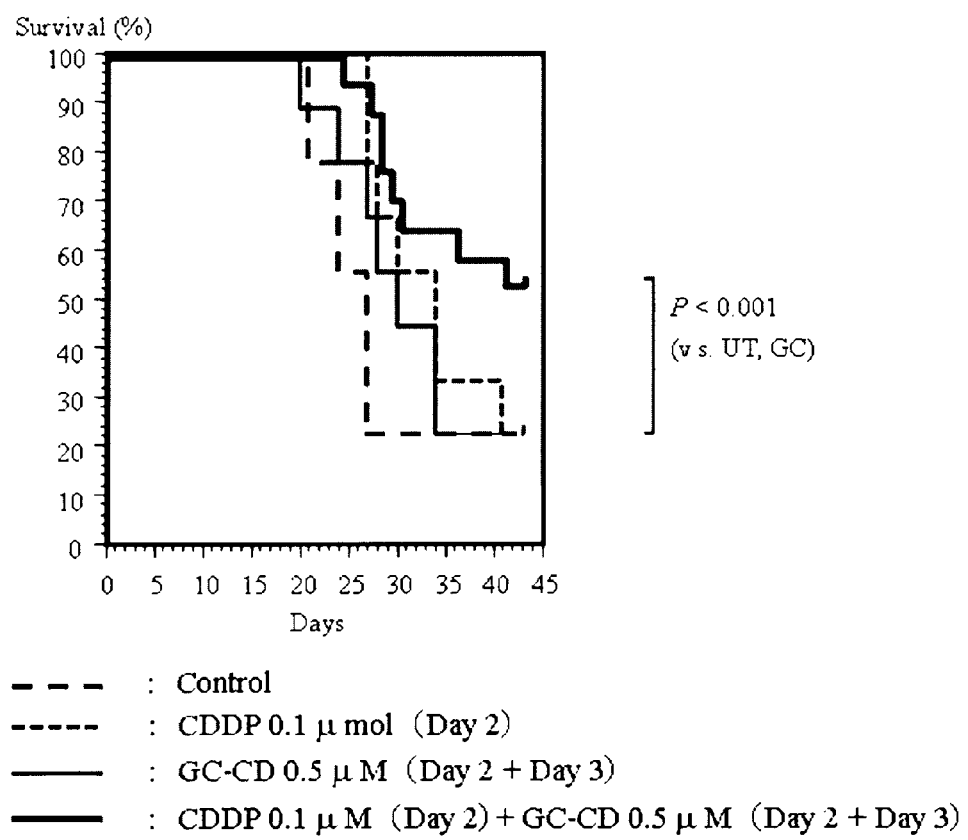
FIG. 7 is a graph showing the survival rate of mice to which colon26 cells were intraperitoneally inoculated, upon single administration of CDDP, GC-CD, or CDDP+GC-CD (single administration of CDDP and double administration of GC-CD, respectively)

FIG. 7 shows the results.

Example 5

Anti-Tumor Effect By Drug Addition

Balb/c mice (6 weeks old, female) were employed as test animals. Colon26 cells ($5\times10^4$ cells/mouse) were subcutaneously inoculated to the mice (day 0). After confirmation that the tumor size reached about 4 mm (day 7 to 10 after inoculation), CDDP and/or GGC-CD was adjusted with physiological saline (Otsuka normal saline) to a concentration of interest, and CDDP, GGC-CD, or CDDP+GGC-CD (200 μL) was administered to the mice through the tail vein, followed by breeding. Time-dependent change in tumor size was monitored to day 21, and the corresponding tumor volume was determined. To the control group, only physiological saline (200 μL) was administered (n=7; 7 mice/group).

Figure 8:
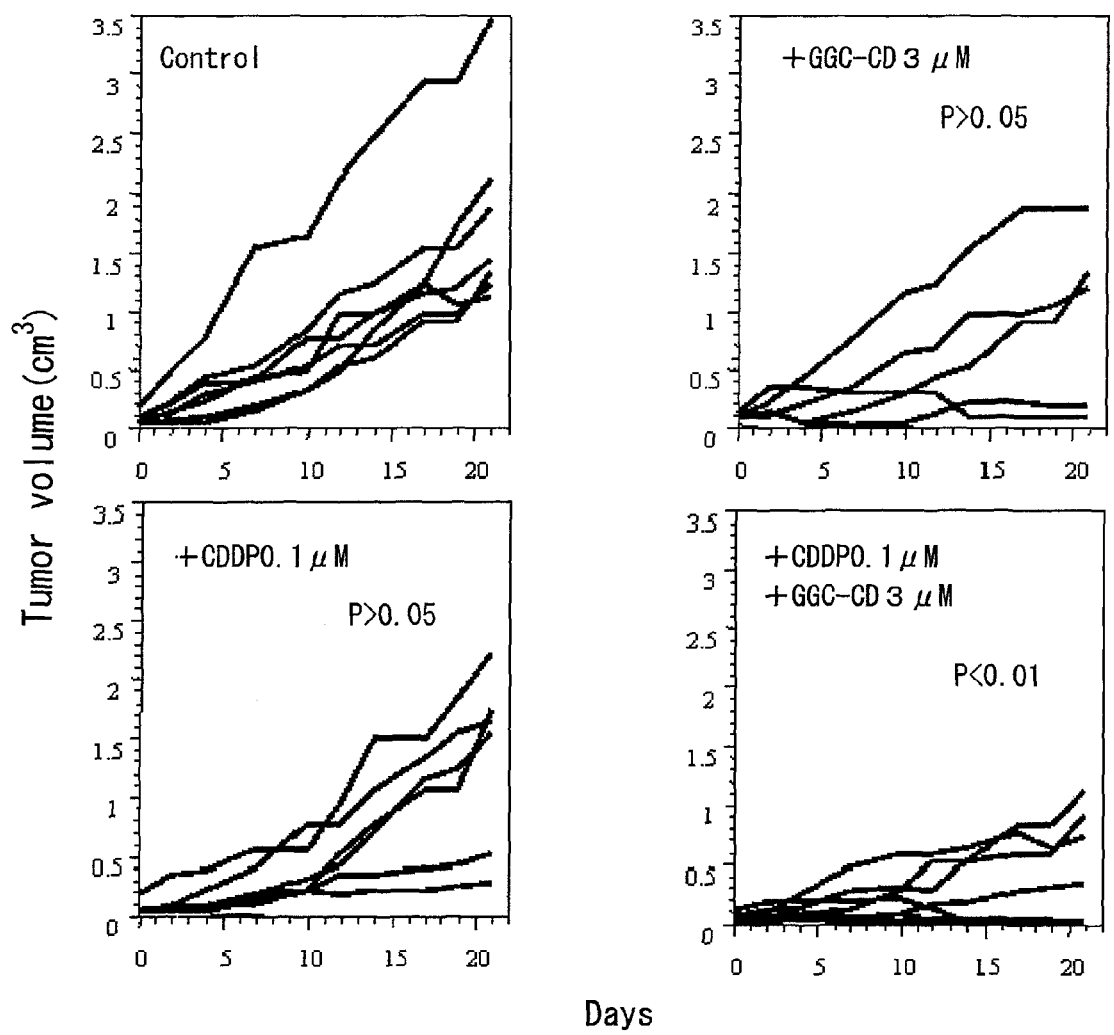
FIG. 8 is a graph showing the effect of suppressing or reducing the tumor growth to which colon26 cells were subcutaneously inoculated in mice, upon single administration of CDDP, GGC-CD, or CDDP+GGC-CD.

FIG. 8 shows the results.

Example 6

Cancer Metastasis Inhibitory Effect By Drug Addition

Balb/c mice (6 weeks old, female) were employed as test animals. Colon26 cells ($5\times10^4$ cells/mouse) were intraperitoneally inoculated to the mice (day 0). Immediately after inoculation, CDDP and/or GC-CD or GGC-CD was adjusted with physiological saline (Otsuka normal saline) to a concentration of interest, and CDDP, GC-CD (or GGC-CD), or CDDP+GC-CD (or GGC-CD) (200 μL) was administered to the mice through the caudal vein, followed by breeding. On day 14, mice were dissected, and the tumor nodes in the lungs were counted. To the control group, no substance was administered (n=10; 10 mice/group).

Figure 9:
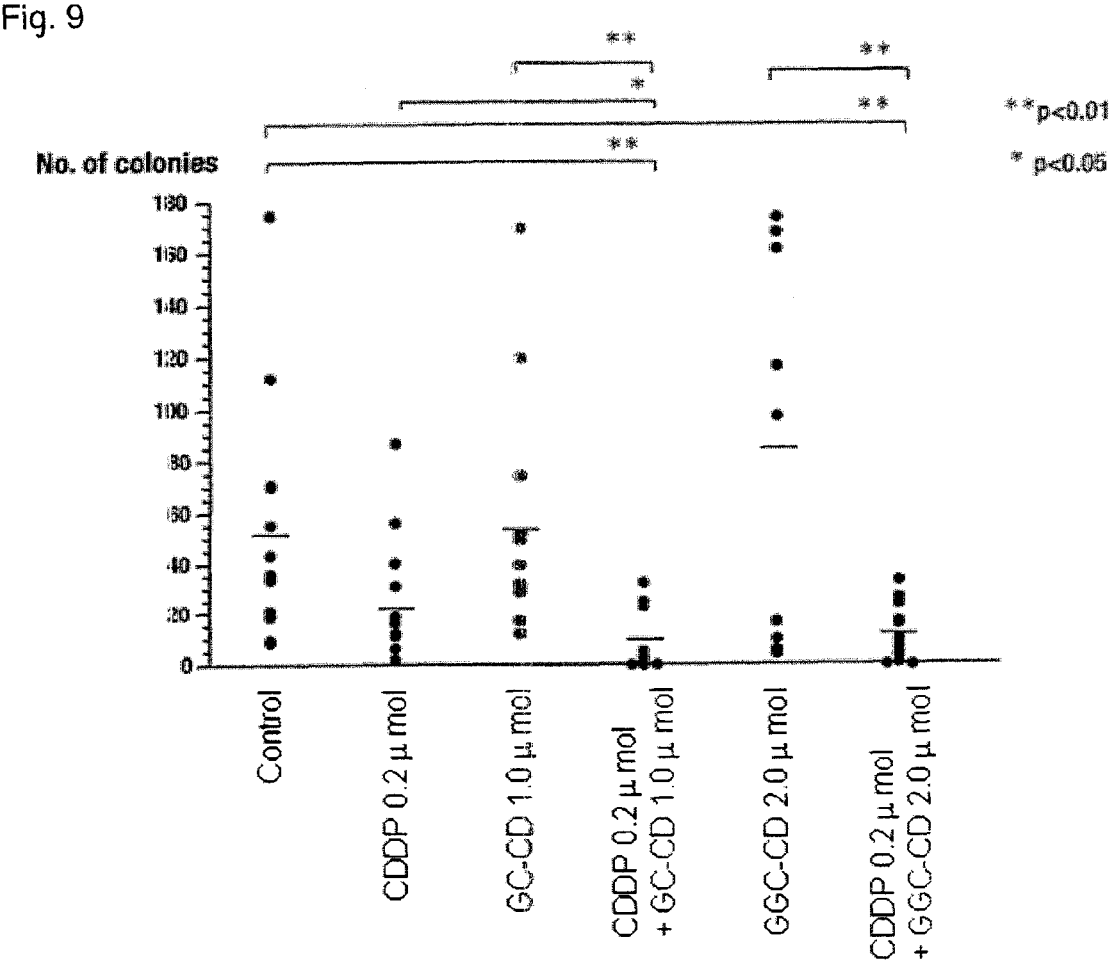
FIG. 9 is a graph showing the effect of inhibiting metastatis of colon26 cells to the lung, upon single administration of CDDP, GC-CD, GGC-CD, CDDP+GC-CD, and CDDP+GGC-CD.

FIG. 9 shows the results.

Example 7

Effect of Drug Addition on Inhibition of Cancer Cell Proliferation

Colon26 cells (derived from mouse colon cancer) were inoculated to a 96-well plate ($1\times10^4$ cells/50 μL, 10% FCS-RPMI medium/well), and incubated at 37° C. for 16 hours. To each well, well-known anti-cancers agent (Oxaliplatin (abbreviated as "L-OHP"), Fluorouracil (5-FU), Paclitaxel (TXL; abbreviated as "PTX"), Docetaxel (TXT; abbreviated as "DTX"), Irinotecan (CPT-11; abbreviated as "CPT"), or Cyclophosphamide (abbreviated as "CPA") and/or a cyclodextrin inclusion compound (abbreviated as "GC-CD") of a cholestanol derivative in which G in formula (1) is GlcNAcβ- (abbreviated as "GC") was added (multi-fold dilution by FCS (−)-medium: final concentration: $\leqq$500 μM, 50 μL), followed by incubation at 37° C. for two days. GC-CD was prepared in accordance with a method disclosed in Example 1(2) in WO 2007/026869. Specifically, a 40% aqueous solution of hydroxypropyl-β-cyclodextrin was prepared, and GC was added to the solution, followed by mixing with stirring (80° C. for 30 minutes), to thereby prepare GC-CD.

As a control, wells to which only FCS(−)-medium had been added were employed. Viable count was performed by means of a cell counting kit (product of Dojin).

Cell proliferation inhibition (CPI) rate (%) was calculated by the following equation. FIG. 10 (FIGS. 10-A and 10-B) shows the results.

$$CPI \text{ rate } (\%) = \left(1 - \frac{\text{treated cells } OD_{450-650}}{\text{untreated cells } OD_{450-650}}\right) \times 100$$

As described hereinabove, through employment, in combination, of the cholestanol derivative of the present invention or a cyclodextrin inclusion compound thereof and an anti-cancer agent, proliferation of various cancer cells is strongly inhibited, and synergistic effect and/or effect of potentiating anti-tumor action of a known anti-cancer agent can be obtained.

What is claimed is:
1. A cancer chemotherapeutic agent comprising, in combination, a cholestanol derivative represented by formula (1):

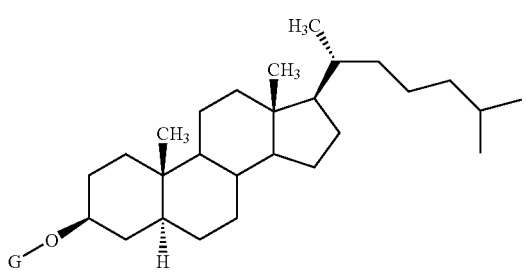

(1)

wherein G represents GlcNAc- or a cyclodextrin inclusion compound thereof, and Cisplatin.

2. The cancer chemotherapeutic agent according to claim 1, which is a compounding agent.

3. The cancer chemotherapeutic agent according to claim 1, which is in the form of a kit including a drug containing a cholestanol derivative and a drug containing Cisplatin.

4. The cancer chemotherapeutic agent according to claim 3, wherein the drug containing a cholestanol derivative is a liposomal formulation.

5. A method of producing a chemotherapeutic agent for the treatment of cancer, the method comprising combining a cholestanol derivative represented by formula (1):

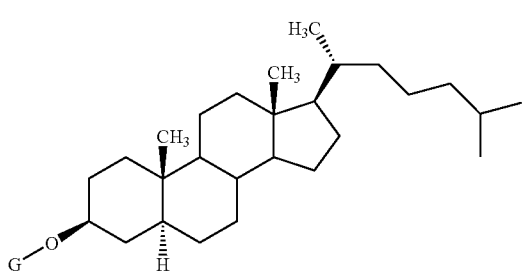

(1)

wherein wherein G represents GlcNAc- or a cyclodextrin inclusion compound thereof and Cisplatin.

6. A colon cancer chemotherapy, comprising simultaneous administering a cholestanol derivative represented by formula (1):

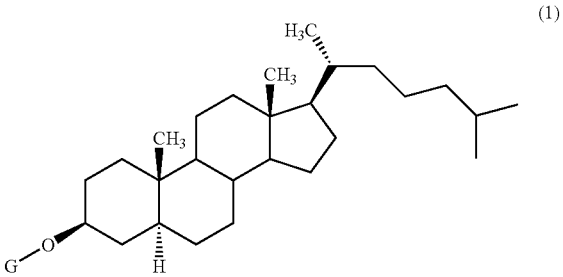

(1)

wherein G represents GlcNAc- or a cyclodextrin inclusion compound thereof and Cisplatin, to a patient in need thereof.

7. The cancer chemotherapy according to claim 6, wherein the drug containing a cholestanol derivative is a liposomal formulation.

\* \* \* \* \*